United States Patent [19]

Glattstein

[11] Patent Number: 4,840,912

[45] Date of Patent: Jun. 20, 1989

[54] PROCESS FOR DRUG DETECTION

[75] Inventor: Baruch Glattstein, Jerusalem, Israel

[73] Assignee: Erez Forensic Technology, Ltd., Israel

[21] Appl. No.: 255,989

[22] Filed: Oct. 11, 1988

Related U.S. Application Data

[62] Division of Ser. No. 12,028, Feb. 9, 1987.

[30] Foreign Application Priority Data

Feb. 12, 1986 [IL] Israel .................................. 77871
Dec. 3, 1986 [IL] Israel .................................. 80860

[51] Int. Cl.$^4$ ...................... G01N 33/00; G01N 33/15
[52] U.S. Cl. ........................................ 436/92; 436/96; 436/901
[58] Field of Search ............................. 436/92, 96, 901

[56] References Cited

U.S. PATENT DOCUMENTS

| | | | |
|---|---|---|---|
| 3,955,926 | 5/1976 | Fischer | 436/92 |
| 4,104,027 | 8/1978 | Carroll | 436/92 |
| 4,110,078 | 8/1978 | Zelonis | 436/92 |

*Primary Examiner*—Barry S. Richman
*Assistant Examiner*—Timothy M. McMahon

[57] ABSTRACT

The invention provides a process for the presumptive identification of cocaine or heroin street drug comprising applying to a sample of the suspected drug a reagent which gives a characteristic color reaction in the presence of trace amounts of organic bases or acetic acid. The invention also provides a prepacked screening kit for illicit cocaine and heroin street drug if present, comprising a reagent which gives a characteristic color reaction in the presence of the trace amounts of organic bases or acetic acid in said illicit substances.

10 Claims, No Drawings

PROCESS FOR DRUG DETECTION

This is a division of application Ser. No. 012,028, filed Feb. 9, 1987.

The present invention relates to a process and test kit for the presumptive identification of cocaine and heroin (diacytylmorphine) street drug.

As will be realized, on numerous occasions a police officer has to determine whether or not a suspected material contains heroin, cocaine or "crack" and thus quickly establish probable cause.

Often, the laboratory is closed, or many miles away, and he has no way of making this determination. A test kit can help an officer detect the presence of such drugs or alternatively to determine that a tested sample definitely isn't one of said drugs.

The quickest test known for drug detection is a color test in which the response of the drugs to a specific reagent makes it possible to assign the drug to one or more classes.

In order to obtain sufficient evidence to detain a suspected drug peddler or drug user, chemical spot test kits have been commercially developed and are used by many law enforcement agencies for the detection of narcotics and drugs of abuse.

Most of the commerical test kits for the identification of heroin are based on the famous Marquis sulfuric acid-formaldehyde reagent which gives a purple violet characteristic color with morphinan structures but not only with morphinan structures.

Clark, "Isolation and Identification of Drugs" Pharmaceutical Press (1969) lists some 46 drugs that all respond in the same way to Marquis reagent. Furthermore, Marquis reagent gives other colors with hundreds of drugs. It is thus apparent that this single color producing reagent cannot really serve for the field identification of drugs, because of the possibility of giving a false positive with other substances of similar structure or similar response characteristics.

The weakness of this single specific reagent test has led to the development of various combination tests which are intended to be used together in a manner which seeks to screen out the false positives and make possible a firm identification of heroin.

In U.S. Pat. No. 4,104,027, an impedimental flowchart is described to identify heroin, suggesting combination of Marquis and Mandelin or Nitric Acid tests. This patent has two disadvantages:
1. It still lacks specificity;
2. Corrosive and harmful liquids such as concentrated sulfuric acid, nitric acid and formaldehyde, are dangerous and impedimental for the user.

In U.S. Pat. No. 3,955,926 there is described a process for the detection of narcotics wherein heroin is detected with a multi-component reagent comprising a solution of benzylamine and iodic acid in dilute acid, and an absorbent support impregnated with ferric chloride, an alkali tartarate and an alkali carbonate. This test however is not specific enough for presumptive identification of heroin.

Similarly most of the commercial test kits for the presumptive identification of cocaine are based on contacting cocaine and its salts with cobalt thiocyanate solutions which results in the formation of a relatively water insoluble turquoise complex.

The relative simplicity of the cobalt thiocyanate test made its use feasible outside the laboratory and created a demand for a variation with increased specifity.

The standard Scott Test (L. J. Scott, Specific Field Test for Cocaine, Microgram VI, 179(1973), used by the customs service, is based on using test tubes in three stages:

A. Using cobalt thiocyanate reagent in a 1:1 water:-glycerine solution that forms the characteristic blue precipitate with cocaine. In this stage, there are still four drugs that will react with the same color reaction as cocaine:
  (1) Phencyclidine (PCP);
  (2) Dibucaine;
  (3) Butacaine;
  (4) Methapyrilene.

The following two stages exclude these four drugs.
  B. Addition of concentrated hydrochloric acid to form a clear pink solution.
  C. Addition of chloroform which turns blue as the complexed cocaine is partitioned into the organic phase.

This method has several disadvantages.
1. Complicated procedure;
2. Non-portable kit;
3. The ratio of solutions of steps (A), (B) is critical;
4. It uses corrosive concentrated hydrochloric acid; and
5. Trace amount of cocaine cannot be detected.

Accordingly, there is still a need for a specific test kit for detection of cocaine and heroin street drug.

Heroin street drug is not a pure chemical but a mixture of heroin, morphine, codeine, paparevine and nescapine salts, trace amounts of their corresponding free bases, traces of acetic acid and some diluents such as sugars, caffeine, phenoborbital and procaine. This is because clandestine laboratories manufacture illicit drugs with no quality control.

In contradistinction thereto, medicinal drugs and pharmaceuticals containing an organic base are manufactured and sold as their pure salts. Manufacture is carried out in the pharmaceutical industry under strict quality control, so that these salts do not contain even trace amounts of free organic bases.

Thus it has been found that 95% of heroin street drug contains trace amounts of free alkaloid bases.

Dogs that are trained to reveal hidden heroin, are trained to detect trace amounts of acetic acid which is also one of the impurities in heroin street drug.

Based on these findings it is now proposed that an efficient way to detect illicit drugs that were synthesized in a clandestine laboratory is to detect trace amounts of free organic base or acetic acid therein.

Thus, contrary to the prior art approaches to the detection of heroin and cocaine, it has now been surprisingly found that a powder suspected of being cocaine base ["crack"] or being street drug heroin can be detected by its organic free base character. Furthermore, street drug heroin can also be identified by the characterizing presence of trace amounts of acetic acid.

Thus in accordance with the present invention there is provided a process for the presumptive detection of cocaine and heroin street drug comprising applying to a sample of the suspected drug a reagent which gives a characteristic color reaction in the presence of trace amounts of organic bases or acetic acid.

Preferably said process is carried out with a sulfonated aromatic pH indicator reagent which produces a color reaction in the presence of trace amounts of acetic acid as well as in the presence of trace amounts of organic free base.

Preferably said sulfonated aromatic pH indicator is selected from the group consisting of bromophenol blue, bromochlorophenol blue and bromocresol green.

As mentioned before, heroin street drug contains trace amounts of organic free base and acetic acid. Furthermore "crack" is cocaine free base and therefore sulfonated aromatic pH indicators which produce a color reaction in the presence of trace amounts of organic free base are also utilizable for the detection thereof. Such indicators as bromophenol blue, bromochlorophenol blue and bromocresol green give intense color when they react with trace amounts of free organic base and/or trace amounts of acetic acid. The preferred indicator is bromophenol blue, which gives an immediate intense violet color with traces of alkaloid bases such as heroin and gives an immediate blue color with cocaine.

Because cocaine free base is the most frequent illicit drug as a free base, a positive blue reaction can be a presumptive detection test for cocaine. It can be further verified by the well known Scott modified cobalt thiocyante reagent.

Thus in its preferred embodiment the present invention provides a test kit for the presumptive identification of cocaine and heroin street drugs comprising a reagent selected from sulfonated aromatic pH indicators which produces a color reaction in the presence of trace amounts of organic free base or acetic acid.

Preferably and reagent is combined with the suspected drug in the presence of a halogenated organic solvent such as dichloromethane, trichloromethane and trichloroethane.

Despite the high effectiveness of the above proposed identification test, it has been found statistically that the sulfonated aromatic pH indicators mentioned above do not react with about 5% of tested samples of heroin street drug (possibly because they were well prepared).

While a test which is accurate in about 95% of the tested samples is already a major improvement in the art, nevertheless it is desirable to provide law enforcement and custom agents with means for also double checking the remaining 5% of samples which might in fact be heroin but which initially test out negative.

In a modification of the simple one reagent test of the present invention there are provided two preferred multireagent tests which allow for positive elimination of a sample as being heroin or cocaine whereby if the results from both tests are negative it can be safely presumed that the sample does not contain cocaine or heroin.

Thus according to one embodiment of the present invention there is provided a multi-reagent test kit for the presumptive identification or elimination of a sample as cocaine or street drug heroin comprising a sulfonated aromatic pH indicator which produces a color reaction in the presence of trace amounts of an organic base or acetic acid as a first reagent and a second reagent which converts salts of organic bases to their corresponding free bases.

Thus in a case wherein the first test comes out negative it is proposed to apply a second reagent to the same sample or to a second one, said second reagent being selected from volatile organic bases such as ammonia and short chain aliphatic derivatives of ammonia, such as mono, di or tri methyl, ethyl, propyl and butyl amines, which turns alkaloids salts to their corresponding bases.

By applying the first reagent once again, a violet color would be presumptive detection of alkaloids, however would be less specific for heroin than the preferred test of applying only the first reagent. If there is no violet color, the suspected powder can be presumed not to contain heroin. If there is a blue color, it is too general to be a presumptive test for an illicit drug; however if there is no blue or violet color at all it can be presumed that the suspected powder does not contain organic base at all.

As an alternative there is also provided according to the present invention a multi-reagent test kit for the presumptive identification or elimination of a sample as cocaine or street drug heroin comprising a sulfonated aromatic pH indicator, which produces a color reaction in the presence of trace amounts of a base or acetic as a first reagent and a second reagent selected from picric acid, styphnic acid and derivatives thereof for forming a hydrophobic yellow colored cocaine or heroin salt.

As is known organic bases or their salts tend to form a highly hydrophobic salt with aromatic compounds having at least one hydroxyl group that functions as the acidic part and electron attracting groups that strongly influence the acidic character of the hydroxy groups such as nitro, cyano, and sulphonic substituents.

However heretofor it has not been suggested to form a colored salt from the reaction of picric or styphnic acid and heroin or cocaine.

Thus picric acid which is a 2,4,6-trinitrophenol and styphnic acid which is a 2,4-dihydroxy-1,3,5 trinitrobenzene are suitable and preferred for use in the present invention.

Furthermore styphnic and picric acid form electron-donor-acceptor charge-transfer (CT) complexes. Some of them are colored complexes. Organic aromatic molecules that have one or two hydroxy groups and several electron attracting substituents that can cause the hydroxy group to function as an acid can be used as an electron acceptor in CT complexes. Polycyclic aromatic molecules without or with electron releasing substituents such as alkyl and alkoxy can form a CT colored complex with the previously defined aromatic acids. CT reactions are usually accomplished in molar ratio.

Picric acid and styphnic acid are phenolic organic acids, and they form CT colored complexes with the following polycyclic aromatic compounds:
Anthracene—Ruby red
Chrysene—Orange red
Pyrene—Dark Red
Benz(a)anthracene—Dark red
Azulene—Brown Violet CT complexes formed with anthracene and its ether derivatives such as dimethyl and diethyl ethers of the following dihydroxy anthracenes: 1,2; 1,5; 1,8; 1,9; 2,3; 2,6; 2,7; 9,10 are preferred and a CT complex of picric acid and anthracene is especially preferred.

When, for example, the picrate CT complex reacts with heroin in anhydrous conditions yellow ammonium picrate salt is immediately formed.

Thus the above acids which are similar in properties, reactions and the characterizing yellow salts which they form with heroin can be used in many ways as described hereinafter with regard to picric acid, it being understood that reagents using styphnic acid are similarly prepared.

The invention can therefore be carried out with regard to the use of the second reagent in the following various ways:

1. Dissolving heroin in a slightly acidic (hydrochloric acid, phosphoric acid) aqueous solution and adding a few drops of aqueous solution of picric acid, a heavy yellow precipitate is formed, which is the hydrophobic heroin picrate salt.

2. Picric acid is slightly colored in organic solvent, such as benzene, chloroform, and dichloromethane. By adding a few drops of such a solution of a suspect substance on a filter paper, an intense yellow lemon salt is formed with slightly colored background.

3. A suspect substance is put on a paper impregnated with picric acid and a few drops of anthracene solution (from a dropper, prepackaged canister or dispenser) are added which stain the paper with red color except the area where there is heroic which turns an intense yellow color.

4. Using paper impregnated with anthracene and anhydrous organic solution of picric acid, a few drops of the solution placed on a sample of the suspect material placed on the reagent impregnated paper to give the desired color reaction.

5. Using paper impregnated with picric acid-anthracene ct complex, a few drops of solvent are placed on a sample of the suspected material placed on the reagent impregnated paper to give an intense yellow color with red background.

In an especially preferred embodiment of the present invention said first reagent is incorporated in a multilayer analytical element comprising an intermediate layer of absorbent substrate impregnated with said reagent, a bottom water-impermeable support layer and an upper hydrophobic protecting layer permeable to heroin dissolved in an organic solvent and impermeable to organic insoluble compounds.

The support layer is preferably polyethylene (Benchkote) [manufactured by Whatman of England]. It has the following characteristics:

1. It prevents humidity from penetrating into the back side of the analytical layer due to the polyethylene support and backing layer provided therein; and 2. It prevents cross contamination by the use of the kit.

The hydrophobic blocking layer is a hydrophobic special glue with the following characteristics:

1. Keeps any humidity from the analytical layer;

2. Sticks the suspected substance to the analytical element; and

3. Prevents passage of organic insoluble compounds while being pemeable to heroin using an organic solvent such as methylene chloride and chloroform, thus reducing the chances of obtaining a false positive to a minimum.

The preferred glues area:
1. 4550 - SB-R (3M Co. U.S.A.);
2. 4910-NF-dissolved in 1,1,1-TCE (3M Co. U.S.A.).

This preferred multilayer analytical element consists of a sheet of cellulose porous matrix in which the analytical layer is between the support and the blocking layer. The suspected substance is placed on the surface of the solid phase blocking layer. By applying dichloromethane on the surface it diffuses into the matrix of the analytical layer and in so doing dissolves the component reagents dispersed therein. When the dry reagent has dissolved, it reacts with the suspected compound to generate a colored product on the surface of the multilayer analytical element.

The performance of the reagents when impregnated in a porous cellulosic matrix are improved by silanizing the filter papers. Silanizing reagents block the hydroxy groups of the cellulose. The filter paper becomes highly hydrophobic (water repellent). The improvements are:

1. Reagents placed on the filter paper are not sensitive to moisture at all;

2. The contrast of the colored reaction and the sensitivity of the reagents based on picric acid when placed on filter paper are improved.

3. The above-mentioned hydrophobic glues can also be applied as a blocking layer to silanized filter paper impregnated with a first reagent based on picric acid.

The preferred silanizing reagents are;
1. Dimethyldichlorosilane;
2. Trimethylchlorosilane; and
3. Dimethylchlorosilane.

The reagents are simply poured on the surface of the paper and air dried.

Both said first and said second reagents can alternatively be packaged in separate aerosol containers and dispensers in combination with a propellant selected from compressed air, a fluorohydrocarbon, a chlorofluorohydrocarbon, $CO_2$ gas, nitrous oxide or $N_2$ gas although simple pump (without propellant) dispensers can also be used.

The concentration of the reagent in organic solvent can range from about 0.1% by weight/volume up to 3% and it is preferred that sufficient reagent be present in the solution so that one spray application will dispense sufficient reagent to bring out the characteristic color reaction with the heroin street drug.

However, as indicated hereinbefore, in an especially preferred embodiment of the present invention both said first and said second reagents are incorporated in a multilayer analytical element comprising an intermediate layer of absorbent substrate impregnated with said reagent, a bottom water-impermeable support layer and an upper hydrophobic protecting layer permeable to heroin or cocaine dissolved in an organic solvent and impermeable to organic insoluble compounds, in which the absorbent substrates are preferably silanized cellulosic matrices.

As discussed hereinbefor if there is no color reaction with said first reagent the invention provides for applying to the same sample or to a second sample, a second reagent comprising a volatile base for forming the corresponding free bases from heroin street drug and then applying once again the first reagent, or applying to a second sample a second alternative reagent selected from picric acid, styphnic acid and derivatives thereof for forming a hydrophobic yellow colored heroin salt.

The above possible sequential tests and presumptive results thereof are illustrated in the following flow chart.

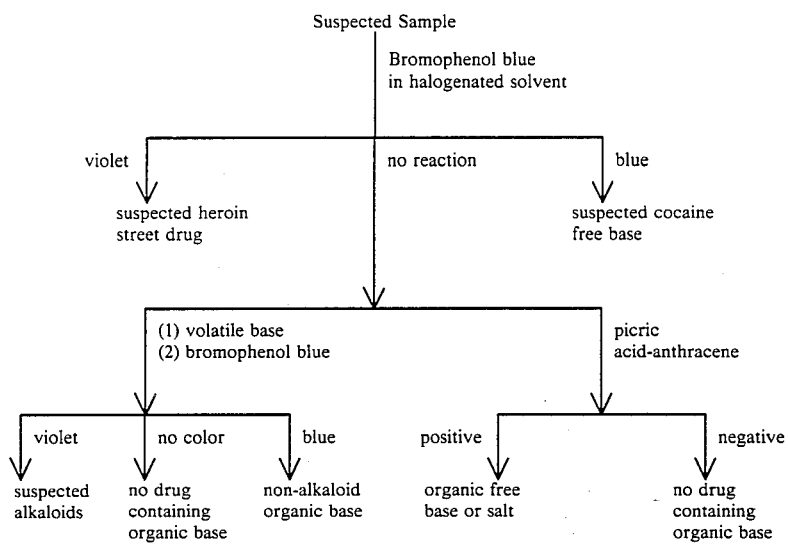

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE 1

A few miligrams of material suspected as heroin street drug are placed on filter paper. A few drops of 5% Bromophenol blue in chloroform are added. A violet color is formed with yellow background thus establishing a strong presumption that the tested sample is indeed heroin.

EXAMPLE 2

First impregnation stage:
Filter paper (Benchkote) was impregnated by dipping into a solution containing 1% bromophenol blue in dichloromethane. Following impregnation, the paper was dried at 60° C. for few minutes.
Second impregnation stage;
The dry impregnated paper from the first stage was then impregnated by spreading a viscous solution of 30% glue (4550-B-R-fsu) in dichloromethane on the impregnated paper.
Test: A few miligrams of a suspected heroin street drug are placed on the glue surface. Adding 2-3 drops of dichloromethane results in the staining of the paper in violet color with yellow background, thus presumptively identifying the sample as heroin.

EXAMPLE 3

The procedure of example 2 was repeated preparing a multilayer analytical element with bromochlorophenol blue as reagent and 4910-NF($3\mu$) as the glue. Wetting of the suspected material with dichloromethane results in the staining of the paper with a violet color with yellow background.

EXAMPLE 4

The procedure of example 2 was repeated preparing a multilayer analytical element with bromocresol green as reagent and 4910-NF($3\mu$) glue. Wetting of the suspected material with dichloromethane results in the staining of the paper with a green color with yellow background.

EXAMPLE 5

The procedure of example 2 was repeated. However the filter paper was first silanized with dimethylchlorosilan. The thus treated analytical element also produced a violet color with yellow background, but with less sensitivity to humidity.

EXAMPLE 6

The impregnation steps of example 2 are repeated. A few miligrams of suspected cocaine base ("crack") are placed on the glue surface. Adding 2-3 drops of dichloromethane results in the staining of the paper in blue color with yellow background.

EXAMPLE 7

The procedure of example 3 was repeated. Wetting of the suspected cocaine base with dichloromethane results in the staining of the paper with a blue color with yellow background.
To later vertify cocaine, the Scott test, in which cobalt thiocyanate reagent in 1:1 water: glycerine solution forms characteristic blue precipitate with cocaine, L.J. Scott, Specific Field Test for Cocaine, Microgram VI, 179 (1983),is used.

EXAMPLE 8

If there is no color reaction in samples tested according to examples 1-5 then there is applied a few drops of 0.01% methylamine in chloroform on the same sample. Once again applying a few drops of 0.5% Bromophenol blue in dichloromethane results in the formation of a violet color with faint blue background which is indicative for heroin samples while no violet color reaction is indicative of non-heroin samples.

EXAMPLE 9

The procedure of examples 1-5 are repeated. If there is no reaction, there is applied on the same sample of suspected heroin street drug a few drops of diethylamine in dichloromethane which results in the formation of a violet color with blue background when the sample is in fact heroin and no violet color when the sample is not heroin.

EXAMPLE 10

The procedure of example 6 was repeated. If there is no reaction there is applied a few drops 0.01% of ammonia in chloroform on the same suspected cocaine sample. If there forms a blue color that does not disappear, it is indication of a salt of an organic base, and the possibility that the sample is cocaine cannot be dismissed and must be further verified in the lab.

EXAMPLE 11

The procedure of example 1 was repeated. If there is no color, a few miligrams of suspected heroin street drug are placed on a filter paper. A few drops of 3% picric acid in chloroform are added. If a yellow color is formed with slightly colored background, it is an indication that the sample is a salt of an organic base and therefor might be pure heroin requiring further laboratory testing. On the other hand a negative result also with this reagent is confirmation that the tested sample is not heroin

EXAMPLE 12

The procedure of example 1 was repeated. If there is no reaction a few drops of 0.5% picric acid-anthracene red complex in dichloromethane (wherein picric acid and the anthracene derivative are present in 1:1 molar ratio) are added. If a yellow color with red background is formed, it is indication for a salt of an organic base with the same presumptions and conclusions as in the previous example.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A process for the screening of suspect samples for the presence of illicit cocaine and street heroin sufficient to institute confiscation of such samples, based upon the presumptive indication of their presence which comprises the steps of applying to samples suspected of containing illicit materials selected from the group consisting of cocaine, cocaine-free-base, or street heroin, a reagent which upon contact with such materials gives a characteristic color reaction to the trace amounts of organic bases or acetic acid commonly present and emitted by said materials, said color reaction providing sufficient indication of the presence of said illicit material for confiscation of said suspect samples prior to positive identification of the individual materials by further tests required for proper prosecution.

2. The process according to claim 1 wherein the applying step is by the application of a solution of said reagent dissolved in a solvent for liquid or aerosol application.

3. The process according to claim 1 wherein said sample, after presumptive identification and confiscation is then subjected to positive identification of the specific illicit substances in the confiscated materials by contacting said material with a second reagent selected from the group consisting of picric acid, styphnic acid, and mixtures, derivatives, and solutions thereof for forming characteristic colored salts by which said substances in said material can be confirmed.

4. The process according to claim 1 wherein a portion of the suspect sample is contacted with a solution of bromophenol blue in a halogenated solvent and if a violet color develops such color indicates the presumptive presence of street drug heroin, if a blue color develops such color indicates the presumptive presence of cocaine; if no color develops said sample portion is contacted with ammonia or a short chain aliphatic volatile base derivative thereof and recontacted with said bromophenol solution reagent to develop colors, violet colors indicating the presence of suspect substances and blue or no color developing indicating innocent substances; if the presence of suspect substance is indicated, then contacting another portion of said suspect sample with a second reagent comprising picric acid, styphnic acid derivatives, mixtures and solutions thereof and if a yellow-colored hydrophobic salt forms there is a confirmation of the presence of heroin, absence of such a yellow salt indicating the absence of heroin in said sample; and the contacting another portion of said sample with the Scott, modified cobalt thiocyanate reagent which forms characteristic blue precipitate with cocaine and exhibits no color change in the absence of cocaine in said sample portion, thus positively identifying any of the aforementioned illicit substances in said suspect material.

5. The process according to claim 1 wherein said reagent is selected from the class of sulfonated aromatic pH indicators which produce a color reaction in the presence of trace amounts of organic bases or trace amounts of acetic acid present in said illicit substances.

6. The process according to claim 5 wherein said indicator is selected from the group consisting of bromophenol blue, bromochlorophenol blue, and bromocresol green.

7. The process according to claim 1 wherein, after the presumptive presence of at least trace amounts of the illicit materials is established by the initial color reaction, said material is further contacted with a reactant which converts any salts of the illicit materials to their corresponding free base for further contact with said reagent to provide a semi-quantitative confirmation indication of the amount of illicit substance present in said suspect material.

8. The process according to claim 7 wherein said reactant is a volatile base.

9. The process according to claim 8, wherein said volatile base is selected from the group consisting of ammonia and short-chained aliphatic derivatives thereof.

10. The process according to claim 9 wherein, when if the initial application of said reagent to said suspect sample is negative, said sample is contacted with said volatile base, and then recontacted with said reagent, absence of color indicating freedom of said sample from illicit materials but the developing of color from said second contacting with the reagent indicating presumptive evidence of an illicit substance sufficient for legal seizure.

* * * * *